US009301704B2

(12) United States Patent
Takai et al.

(10) Patent No.: US 9,301,704 B2
(45) Date of Patent: *Apr. 5, 2016

(54) MAGNETIC RESONANCE IMAGING SYSTEM FOR NON-CONTRAST MRA AND MAGNETIC RESONANCE SIGNAL ACQUISITION METHOD EMPLOYED BY THE SAME

(75) Inventors: Hiroshi Takai, Nasushiobara (JP); Yoshimori Kassai, Nasushiobara (JP)

(73) Assignees: KABUSHIKI KAISHA TOSHIBA, Minato-Ku, Tokyo (JP); TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1980 days.

This patent is subject to a terminal disclaimer.

(21) Appl. No.: 11/090,852

(22) Filed: Mar. 25, 2005

(65) Prior Publication Data

US 2006/0100503 A1    May 11, 2006

(30) Foreign Application Priority Data

Mar. 26, 2004  (JP) ................................. 2004-092677

(51) Int. Cl.
*A61B 5/05* (2006.01)
*A61B 5/055* (2006.01)

(52) U.S. Cl.
CPC ..................................... *A61B 5/055* (2013.01)

(58) Field of Classification Search
CPC .................................. A61B 5/055; A61B 5/05
USPC .......... 600/410, 413, 419; 324/307, 309, 318, 324/322
See application file for complete search history.

(56) References Cited

U.S. PATENT DOCUMENTS

| 4,718,424 | A | * | 1/1988 | Nishimura | ..................... | 600/419 |
| 4,836,209 | A | * | 6/1989 | Nishimura | ..................... | 600/419 |
| 4,993,414 | A | * | 2/1991 | Macovski et al. | ............. | 600/419 |
| 5,031,624 | A | * | 7/1991 | Mistretta et al. | .............. | 600/419 |

(Continued)

FOREIGN PATENT DOCUMENTS

| JP | 2000-005144 | 1/2000 |
| JP | 2005-528175 | 9/2005 |

(Continued)

OTHER PUBLICATIONS

Shreyas S. Vasanawala et al., Prospective MR Signal-Based Cardiac Triggering; Magnetic Resonance in Medicine 42:82-86 (1999).*

(Continued)

*Primary Examiner* — Bo J Peng
(74) *Attorney, Agent, or Firm* — Nixon & Vanderhye P.C.

(57) ABSTRACT

A magnetic resonance imaging system uses a first RF coil for acquiring a magnetic resonance signal from a subject, and a device for estimating a cardiac phase of the subject based on the magnetic resonance signal acquired by the first RF coil. The first RF coil, for example, can be an RF coil exclusive to cardiac phase estimation. The magnetic resonance imaging system also uses a second RF coil for acquiring a magnetic resonance signal based on the estimated cardiac phase, and a device for reconstructing a magnetic resonance image of the subject based on the magnetic resonance signal acquired by the second RF coil. Thus, MRA can be performed by estimating a cardiac phase.

12 Claims, 7 Drawing Sheets

(56) References Cited

U.S. PATENT DOCUMENTS

| | | | |
|---|---|---|---|
| 5,311,134 A * | 5/1994 | Yamagata et al. | 324/318 |
| 5,377,680 A * | 1/1995 | Bernstein et al. | 600/413 |
| 5,435,303 A * | 7/1995 | Bernstein et al. | 600/413 |
| 5,777,473 A * | 7/1998 | Takai et al. | 324/309 |
| 5,830,143 A * | 11/1998 | Mistretta et al. | 600/420 |
| 5,997,883 A * | 12/1999 | Epstein et al. | 324/306 |
| 6,650,115 B2 * | 11/2003 | DiCarlo et al. | 324/307 |
| 6,922,580 B2 * | 7/2005 | DeMeester et al. | 600/413 |
| 7,026,818 B2 * | 4/2006 | Machida et al. | 324/322 |
| 7,254,437 B2 * | 8/2007 | Miyazaki | 600/410 |
| 7,382,132 B1 * | 6/2008 | Mathew et al. | 324/318 |
| 7,613,496 B2 * | 11/2009 | Miyazaki et al. | 600/419 |
| 2002/0032376 A1 * | 3/2002 | Miyazaki et al. | 600/410 |
| 2002/0087068 A1 * | 7/2002 | Foo | 600/413 |
| 2002/0156367 A1 * | 10/2002 | Pettersson et al. | 600/413 |
| 2003/0042905 A1 * | 3/2003 | Miyazaki et al. | 324/314 |
| 2003/0050552 A1 * | 3/2003 | Vu | 600/410 |
| 2003/0132750 A1 * | 7/2003 | Machida et al. | 324/322 |
| 2003/0225328 A1 * | 12/2003 | DeMeester et al. | 600/419 |
| 2004/0155653 A1 * | 8/2004 | Larson et al. | 324/309 |
| 2004/0186372 A1 * | 9/2004 | Boernert et al. | 600/410 |
| 2007/0167725 A1 * | 7/2007 | Tropp et al. | 600/410 |
| 2014/0051978 A1 | 2/2014 | Takai et al. | |

FOREIGN PATENT DOCUMENTS

| | | |
|---|---|---|
| JP | B4820567 | 11/2011 |
| WO | 03/102618 A1 | 12/2003 |

OTHER PUBLICATIONS

Cardiovascular MR imaging: Pressure-gating using the arterial pressure signal from a conventional ferromagnetic micromanometer-tip catheter; Magnetic Resonance Imaging, vol. 12, Issue 3, pp. 531-534 (1994).*

Vasanawala et al., "Prospective MR signal-Based Cardiac Triggering", Magnetic Resonance in Medicine 42:82-86 (1999).

Kim et al., "Extraction of Cardiac and Respiratory Motion Cycles by Use of Projection Data and Its Applications to NMR Imaging", Journal of Magnetic Resonance 25-37 (1990).

JP Office Action dated May 27, 2014 in JP 2013-204295.

J.P. Ridgway, et al., "Multiple phase, black-blood imaging of the heart using real-time acquisition: Initial results.", Proc. Intl. Soc. Mag. Reson. Med. 6, US, Apr. 18, 1988, p. 815.

JP Office Action dated Jul. 30, 2013 in JP 2012-221065.

B. Schneider, et al., "Left Ventricular Phase Contrast Velocity Mapping in 34 Patients with Ischaemic Heart Disease," Proc. Intl. Soc. Mag. Reson. Med 8, U.S.A., Apr. 1, 2000, p. 214.

Japanese Office Action mailed Mar. 29, 2011, re JP 2005-092783.

* cited by examiner

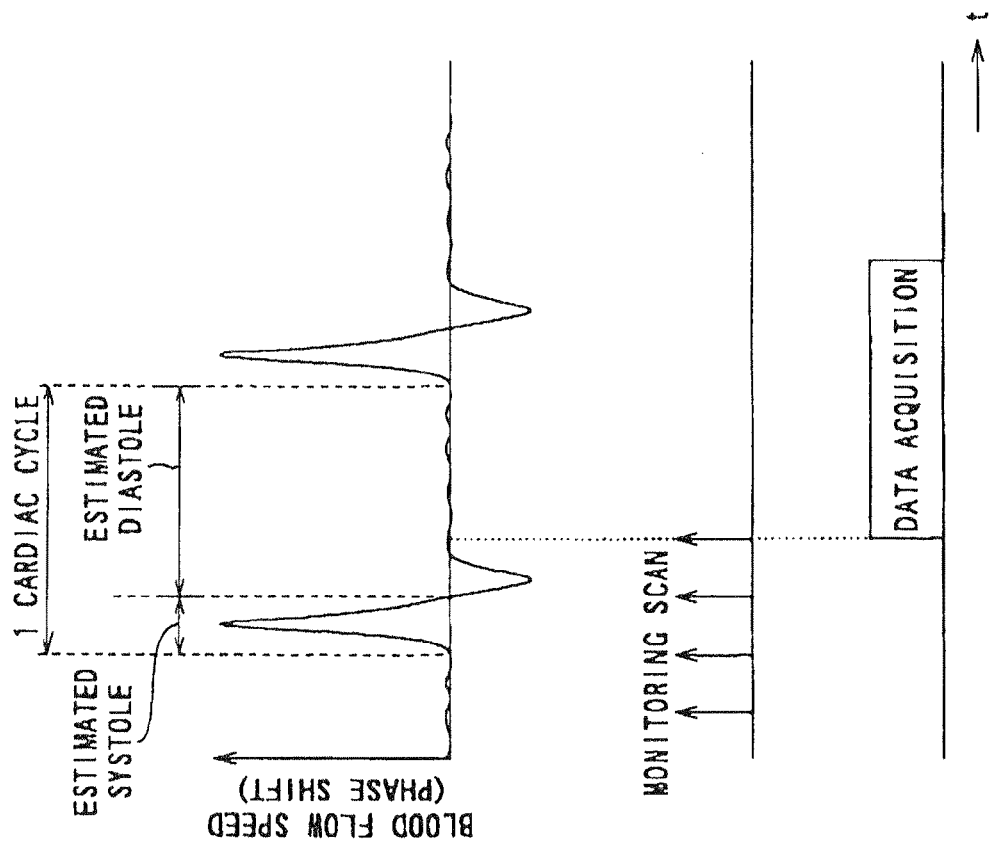

MAGNETIC RESONANCE IMAGING SYSTEM FOR NON-CONTRAST MRA AND MAGNETIC RESONANCE SIGNAL ACQUISITION METHOD EMPLOYED BY THE SAME

BACKGROUND OF THE INVENTION

1. Technical Field of the Invention

The present invention relates to a magnetic resonance-imaging system for medical use and a magnetic resonance signal acquisition method. More particularly, the present invention relates to a magnetic resonance imaging system which does not use an electrocardiographic (ECG) synchronizer per se, but substantially enables non-contrast MRA (MR Angiography) under ECG-gated trigger scanning and to a magnetic resonance signal acquisition method employed by the system.

2. Related Art

A magnetic resonance (MR) imaging is an imaging technique for magnetically exciting nuclear spin of a subject placed in a static magnetic field by using a high-frequency signal of Larmor frequency, and for reconstructing an image by using an MR signal generated with the excitation. Such magnetic resonance imaging systems implementing this imaging method have now become essential medical modalities.

In magnetic resonance imaging diagnosis for medical use, one of the important imaging techniques is MRA for depicting a blood vessel image of a subject. The MRA, for one thing, may be classified into contrast MRA and non-contrast MRA depending on whether or not a contrast medium is administered to a subject in carrying out the diagnosis.

The contrast MRA is an imaging technique in which MR scan is performed by administrating a contrast medium to a subject. This technique, however, casts a large mental and physical burden on a subject because an invasive treatment is required to be given to the subject in administrating the contrast medium. In addition, the cost for such an examination is expensive. On occasion, a contrast medium cannot even be administered to a subject depending on the constitution or the like of the subject. Therefore, use of non-contrast MRA is desired from the clinical viewpoint.

One of such non-contrast MRA techniques is performed by reflecting water components in blood. Japanese Unexamined Patent Application Publication No. H11-338409 discloses a technique included in this category, i.e., a SPEED (Swap Phase Encode Extended Data) technique, in which lung blood vessels having comparatively high flow speed are depicted utilizing the blurring of T2 relaxation time of blood. Japanese Unexamined Parent Application Publication No. H11-047155 discloses an FBI (Fresh Blood Imaging) technique, in which blood pumped out from the heart is scanned in a time phase of comparatively stable blood flow speed using an ECG synchronization technique.

These SPEED and FBI techniques have as their bases an FSE (Fast SE) technique. Thus, when the influence of the motion of a subject, which has been caused between echoes, on data acquisition is largely varied ghosts are likely to occur on a reconstructed image, thereby deteriorating image quality. It is important, therefore, that scanning is performed in a time phase when blood flow speed has been stabilized. In particular, when arteries are depicted, scanning should be performed in a time phase when a blood flow speed is comparatively low (i.e., the diastolic phase in a cardiac cycle). Accordingly, parallel use of the ECG synchronization technique is indispensable.

However, as taught by the foregoing known references, for the non-contrast MRA techniques by which the ECG synchronization technique is essential, a plurality of electrodes for detecting a signal of an ECG synchronizer are required to be stuck onto a subject, arising in problems, resolutions for which have been sought. Specifically, sticking a plurality of electrodes onto a body surface of a subject creates a heavy burden on an operator preparing for magnetic resonance imaging. For a subject, or a patient, as well, this sticking of electrodes may increase a mental and physical burden. Moreover, a gradient magnetic field signal for scanning may be superimposed on an ECG signal detected by the electrodes, which probably causes turbulence in the waveform of the detected ECG signal. If the turbulence in the ECG waveform becomes prominent, detection of the R wave may become difficult. This may deteriorate the quality of a reconstructed image, and require time, more than necessary, for scanning in the magnetic resonance imaging technique, necessitating one to start over preparation for setting, scanning and the like again and again. As a result, patient throughput is decreased.

SUMMARY OF THE INVENTION

This invention has been made in view of the problems of the non-contrast MRA combined with the conventional ECG synchronization technique described above, and has as its object to provide a magnetic resonance imaging system for non-contrast MRA and a magnetic resonance signal acquisition method, which can mitigate the burden imposed on a subject resulting from the use of the ECG synchronization technique, and can reduce deterioration of image quality and increase patient throughput.

In order to achieve the object, the magnetic resonance imaging system related to one aspect of the present invention is provided with: a first RF coil for acquiring a magnetic resonance signal from a subject; a device for estimating a cardiac phase of the subject based on the magnetic resonance signal acquired with the first-RF coil; a second RF coil for acquiring a magnetic resonance signal from the subject based on the estimated cardiac phase; and a device for reconstructing a magnetic resonance image of the subject based on the magnetic resonance signal acquired with the second RF coil.

The magnetic resonance Imaging system related to another aspect of the present invention is provided with: a first scanning device for acquiring a magnetic resonance signal from a subject and estimating a cardiac phase of the subject based on the magnetic resonance signal; a second scanning device for acquiring a magnetic resonance signal of a plurality of time phases of the subject based on the cardiac phase obtained by the first scanning means; a device for producing a plurality of preparatory images from the magnetic resonance signal obtained by the second scanning means; a device for designating at least one image from the plurality of preparatory images; and a third scanning device for acquiring a magnetic resonance signal from the subject in a time phase corresponding to the designated image.

The present invention provides a magnetic resonance signal acquisition method as one aspect, which comprises: a step of estimating a cardiac phase of a subject based on a magnetic resonance signal acquired from a first region of the subject using a first RF coil; and a step of providing the information on the estimated cardiac phase to means for acquiring a magnetic resonance signal for imaging from a second region of the subject using a second RF coil.

BRIEF DESCRIPTION OF THE DRAWINGS

In the accompanying drawings:

FIGS. 4A to 4C are explanatory diagrams showing a relation between blood flow speed in the cardiac chamber, and monitoring scan and data acquisition;

DETAILED DESCRIPTION OF THE PREFERRED EMBODIMENTS

Some embodiments of the magnetic resonance imaging system related to the present invention will now be described with reference to the accompanying drawings.

First Embodiment

Referring to FIGS. 1 to 4, description is provided on the first embodiment of the magnetic resonance imaging system and a magnetic resonance signal acquisition method related to the present invention.

Figure 1:
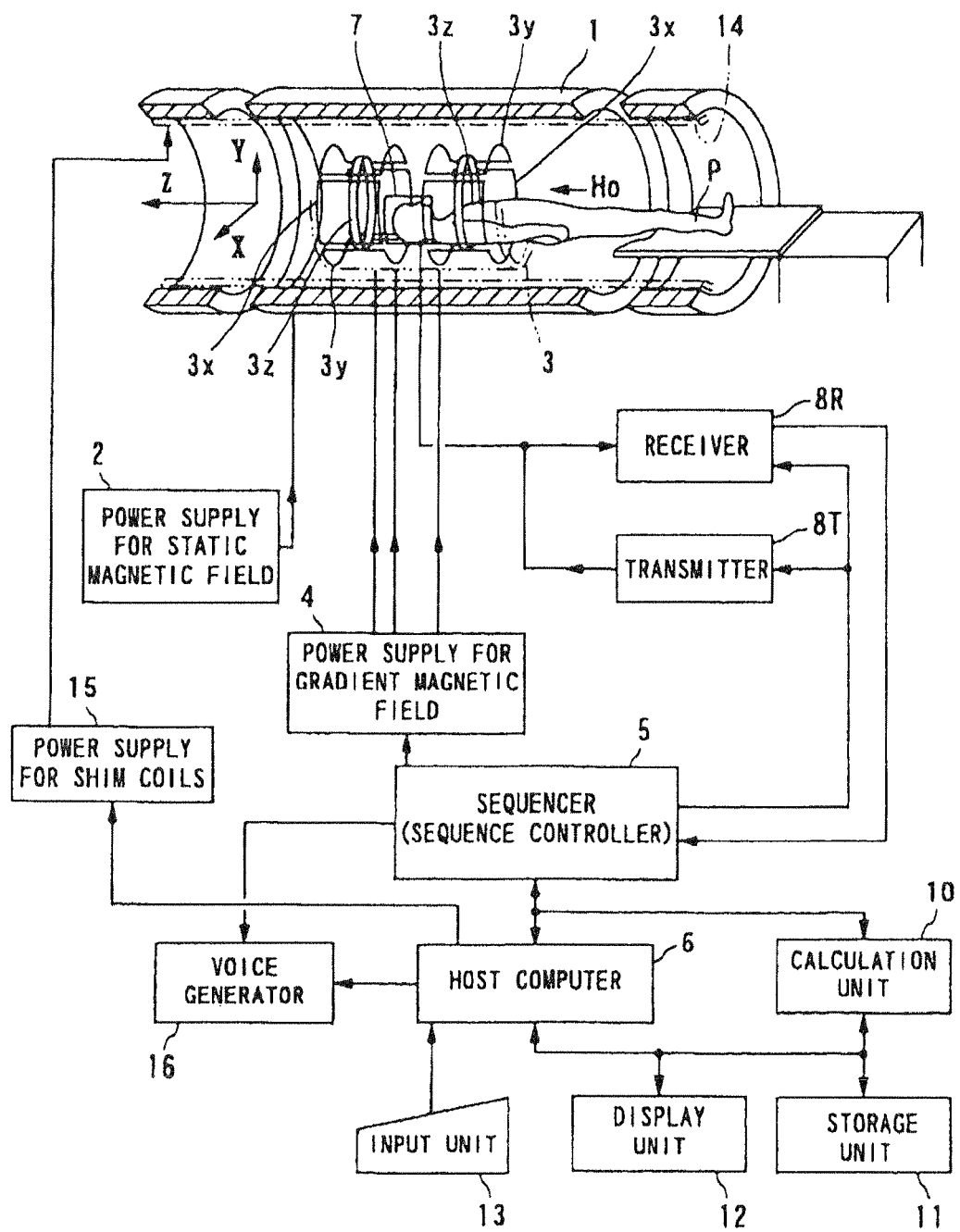
FIG. 1 is a schematic block diagram showing a configuration of the magnetic resonance imaging system related to a first embodiment of the present invention.

FIG. 1 schematically shows a configuration of the magnetic resonance imaging (MRI) system in the first embodiment.

The magnetic resonance imaging system comprises a table section for placing a subject P to be examined, a static magnetic field generating section for generating a static magnetic field, a gradient magnetic field generating section for adding position information to the static magnetic field, a transmitter-receiver section for transmitting and receiving a high-frequency signal, and a control-operation section for taking on control of the entire system and image reconstruction.

The static magnetic field generating section comprises, for example, a superconducting magnet 1, and a power supply 2 for static magnetic field for supplying power to the magnet 1, and generates a static magnetic field $H_O$ in the axial direction (Z axis direction) of a cylindrical opening (diagnostic space) into which the subject P is insertedly placed. Note that a shim coil 14 is provided to the magnet portion. Current for uniforming the static magnetic field is supplied to the shim coil 14 from a power supply 15 for the shim coil, under the control of a host computer which will be described later. The table section is so arranged that a top plate carrying the subject P can be inserted into and retreat from the opening of the magnet 1.

The gradient magnetic field generating section comprises a gradient magnetic field coil unit 3 which is incorporated into the magnet 1. The gradient magnetic field coil unit 3 comprises three pairs (types) of x, y and z coils 3x-3z for generating gradient magnetic fields in an X-axis direction, a Y-axis direction and a Z-axis direction which are orthogonal to each other. The gradient magnetic field portion also comprises a power supply 4 for gradient magnetic field for supplying power to the x, y and z coils 3x-3z. The power supply 4 for gradient magnetic field supplies pulsed current for enabling the x, y and z coils 3x-3z to generate gradient magnetic fields, under the control of a sequencer 5 which will be described later.

By controlling the pulsed current supplied to the x, y and z coils 3x-3z from the gradient magnetic field power supply 4, the gradient magnetic fields in the directions of physical axes, i.e., three axes (X axis, Y axis and Z axis), can be composed to establish and change any logical axis consisting of a gradient magnetic field $G_S$ in a slice direction, a gradient magnetic field $G_E$ in a phase-encoding direction, and a gradient magnetic field $G_R$ in a read-out direction (frequency-encoding direction), which are orthogonal to each other. The individual gradient magnetic fields in the slice direction, the phase-encoding direction and the read-out direction are superimposed on the static magnetic field $H_O$.

The transmitter-receiver section comprises an RF coil 7 which is disposed in the vicinity of the subject P in an imaging space in the magnet 1, and a transmitter 8T and a receiver 8R which are connected to the coil 7. The transmitter 8T and the receiver 8R operate under the control of the sequencer 5 which will be described later. With the operation, the transmitter 8T supplies an RF current pulse at Larmor frequency for exciting nuclear magnetic resonance (NMR), The receiver 8R fetches an MR signal (high-frequency signal) received by the RF coil 7, imparts the signal with several signal processings, such as preamplification, intermediate frequency conversion, phase detection, low-frequency amplification and filtering, and then effects A/D conversion to produce a digital data (original data) of the MR signal.

The control-operation section comprises the sequencer (also referred to as a sequence controller) 5, a host computer 6, a calculation unit 10, a storage unit 11, a display 12, an input unit 13 and a voice generator 16. The host computer 6 gives a command related to pulse sequence information to the sequencer 5 in accordance with a stored software procedure (not shown), and has a function of performing overall control of the device.

The sequencer 5 comprises a CPU and memories, and is so arranged to store the pulse sequence information transmitted from the host computer 6, control the operations of the gradient magnetic field power supply 4, the transmitter 8T and the receiver 8R, and input the digital data of the MR signal outputted from the transmitter 8R for transmission to the calculation unit 10. The pulse sequence information here is intended to mean all the information required for operating the gradient magnetic field power supply 4, the transmitter 8T and the receiver 8R in accordance with a series of pulse sequences, including, for example, information related to the intensity, duration of application, timing of application and the like of a pulse current to be applied to the x, y and z coils 3x-3z.

The pulse sequences are for two dimensional (2D) scan or three dimensional (3D) scan, and the features of the pulse train may be of various types based, for example, on a GE (gradient echo) technique, an FFE (fast FE) technique, an SE (spin echo) technique, an FSE (fast SE) technique, an FASE (Fast Asymmetric SE) technique and an EPI (Echo Planar Imaging) technique. Alternatively, features obtained by effecting a segmented technique to the pulse trains based on these techniques, may also be employed.

The calculation unit 10 inputs, through the sequencer 5, the digital data (also referred to as the original data or the raw data) outputted from the receiver 8R, arranges the digital data in a two-dimensional or three-dimensional k space (also referred to as Fourier space or a frequency space) defined by the internal memory, and subjects every set of the data to two-dimensional or three-dimensional Fourier conversion for reconstruction as an image data in a real space. The calculation unit is also enabled to execute composite processing and difference calculation processing of data related to an image, as required. The composite processing includes, for example, an addition process for every pixel and a maximum intensity projection (MIP) process. Other examples of such composite processing may include a process in which axes of a plurality of frames are matched with each other in Fourier space for composition into one original data of one frame with the original data being left as it is. Note that the addition process includes a simple addition process, an addition averaging process and a weighted addition process.

The storage unit 11 can store image data subjected to the composite processing and the difference calculation processing described above, as well as a reconstructed image. The display 12 is used, for example, for indicating a reconstructed image. Such information, as desired by an operator, for example, on parameter, scanning conditions, pulse sequences, image composition and difference calculation can be inputted to the host computer 6 through the input unit 13.

When a command is received from the host computer 6, the voice generator 16 can dispatch messages for starting and stopping breathing in the form of voice.

In the present embodiment, although no mechanism is employed for obtaining an ECG signal from a subject by actually using an ECG (electrocardiographic) measuring device, the present embodiment is adapted to carry out a pseudo imaging scan with electrocardiographic synchronization. For this purpose, it is required to obtain a signal or information, i.e. an indicator, based on which a cardiac phase of a subject can be estimated. Such a signal or information used in the present invention includes, for example, variation in the blood flow speed in the cardiac chamber (i.e., variation in the phase shift amount of spin imparted to blood flow), variation in an MR signal value obtained from the heart (cardiac chamber), and variation in the size of the cardiac chamber. In the following description, the variation in the blood flow speed in the cardiac chamber is used as the indicator for estimating a cardiac phase of a subject. In short, in the present embodiment, a pseudo imaging can be performed with the electrocardiographic synchronization technique utilizing the data showing periodic variation of the blood flow speed.

Figure 2:
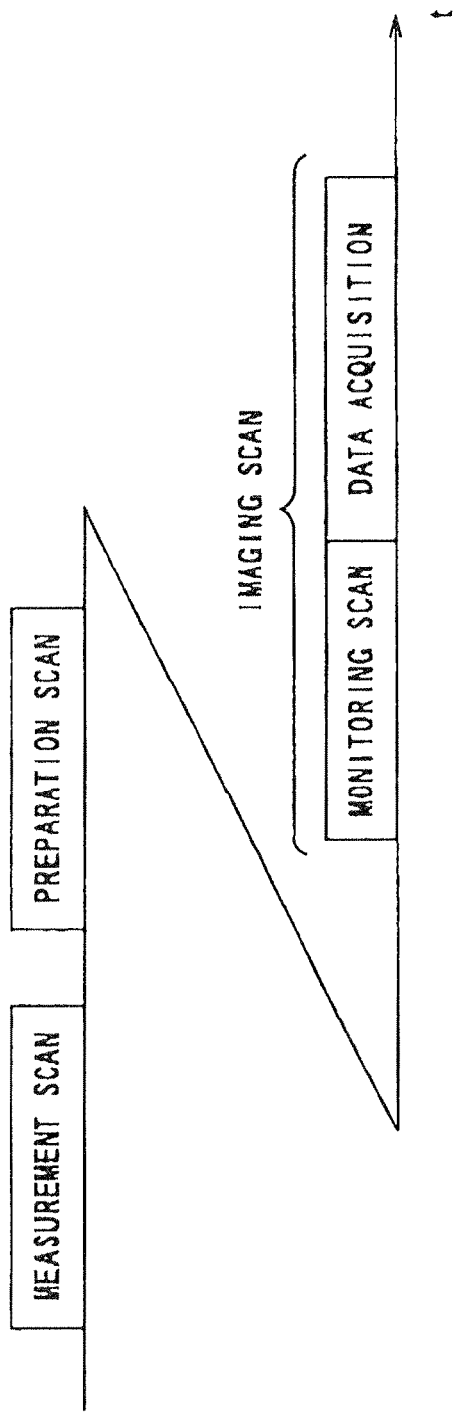
FIG. 2 is an explanatory diagram showing a chronological order of a measuring scan, a preparing scan and an Imaging scan employed in the first embodiment.

In carrying out imaging, as shown in FIG. 2, the host computer 6 sequentially performs the measuring scan, the preparing scan and the imaging scan. The imaging scan includes monitoring scan.

The measuring scan is a scan for measuring in advance the relation of a cardiac phase to a blood flow speed in the cardiac chamber of a subject, the speed serving as an indicator of the cardiac phase, to determine a timing in the diastole of a cardiac cycle. In the present embodiment, speed encoding of blood flow is performed along the long axis of the cardiac chamber by using a phase contrast (PC) technique, while continuingly measuring the variation in the blood flow speed at a desired ROI position on the long axis, so as to obtain a data indicating the variation of the blood flow speed corresponding to the individual cardiac phases (i.e., individual timings in the cardiac cycle). The data showing the variation in the blood flow speed, which has been obtained by this scan, enables determination as to which timing of the cardiac cycle the systole and diastole constituting the cardiac cycle correspond to. As a result, the timing of the diastole can be specified as time from a certain reference position (e.g., a peak which is repeated in a waveform which indicates varying data).

Note that the measuring scan does not necessarily have to be performed at the time of imaging, but may be performed prior to the imaging. However, in the present embodiment, since the variation in the cardiac cycle is estimated based on the blood flow speed, and from the view point of estimating the actual cardiac phases of a subject as accurately as possible, the measuring scan should preferably be performed immediately before the imaging.

The preparing scan is a scan for confirming the depiction of blood flow which is performed in each of a plurality of designated time phases, including the diastole in the periodic variation in the blood flow speed. Specifically, a two-dimensional scanning is performed in the plurality of time phases to reconstruct a plurality of two-dimensional images for indication on the display 12. The preparing scan includes blood flow measuring scan by using the PC technique for detecting a time phase, i.e., a timing, for starting the preparing scan.

The reason for finishing the preparing scan with the two-dimensional scan is that the preparing scan is used only for confirming the degree of depiction of the blood flow. Accordingly, two-dimensional scan is used since it may much shorten the scanning time. It is desirable that the type of the pulse sequence used for the preparing scan may be the same as the one used for the imaging scan. This is because, in doing so, the depiction of the blood flow can be observed in a state close to that in the actual imaging. The preparing scan should desirably be performed with respect to the same site as the one imaged in the imaging scan as will be described later, or the site including the same desired region as the one imaged in the imaging scan.

The plurality of images obtained in the preparing scan are indicated on the display 12 as an example for visual confirmation by an operator. This may allow an operator to designate, through the input unit 13, the best contrast image depicting the blood flow to be observed. This designation information is provided to the host computer 6, and thus the host computer 6 can recognize at which value (i.e., cardinal phase), in the varying data of the blood flow speed, the designated image has been acquired. In other words, as a result of the preparing scan, the host computer 6 can retain a specific time phase in the diastole of the cardiac cycle as a set value of the blood flow speed.

The set value of the blood flow speed that has been set in this way serves as an amount corresponding to a specific time delay from the R wave, for example, as a reference wave in the ECG waveform. Accordingly, by providing this set value, the imaging scan can be started at the specific cardiac phase (i.e., at the data acquisition timing) in the diastole.

Note that the preparing scan should not necessarily be essential. Specifically, an operator may designate a desired value of the blood flow speed as can be obtained from the operator's experience in the past, through the input unit 13, without performing the preparing scan. Alternatively, such a designation or the preparing scan may be optionally selected on a case-by-case basis.

Finishing through the preparation in this way, the imaging scan can be performed. In order to carry out data acquisition (main scan) by the imaging scan, the desired specific cardiac phase (the set value of the blood flow speed) in the diastole, as described above, is required to be detected. For detecting this, the monitoring scan is started prior to the data acquisition. The monitoring scan is carried out by performing speed encoding of a pulse train with the phase contrast (PC) technique, for example, at a specific interval (e.g., 100 ms) along the long axis of the cardiac chamber. Thus, the blood flow speed at a desired ROI portion of the cardiac chamber can be obtained at a specific interval. This speed is compared with the set-value (i.e., data acquisition timing that has been set as described above) of the blood flow speed stored in advance. As a result of this comparison, when both of them match with each other, or it is determined that both are considered to match with each other, data acquisition is started. The data acquisition is performed using a three-dimensional pulse sequence.

Hereinafter is described an entire operation and its effects of the present embodiment.

As shown in FIG. 2, the measuring scan and the preparing scan are to be performed prior to the imaging scan.

Figure 3:
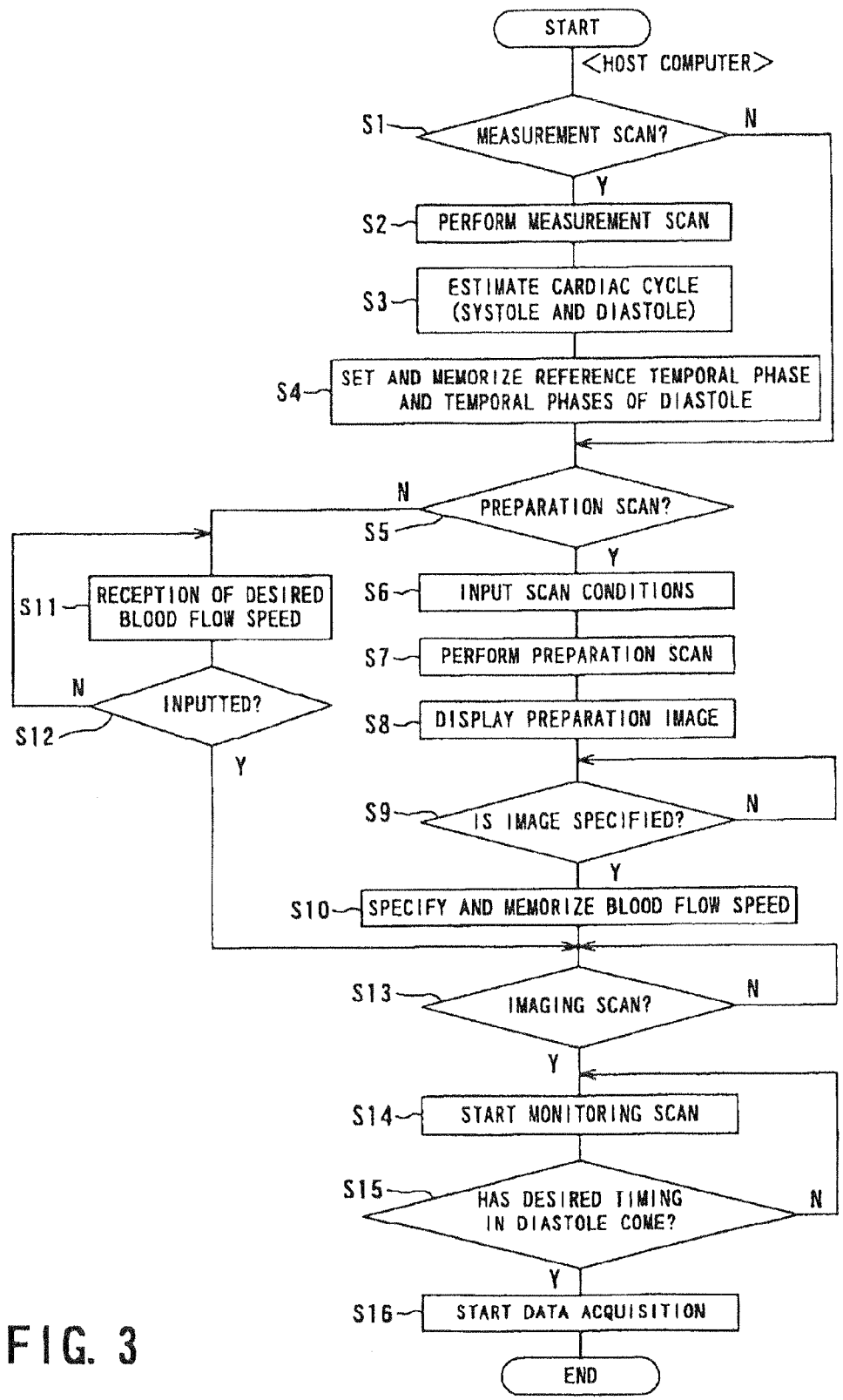
FIG. 3 is a schematic flow diagram showing a process of scanning executed by a host computer.

The host computer 6 sequentially performs the processes outlined in FIG. 3 to execute the measuring scan, the preparing scan and the imaging scan.

The host computer 6 determines first whether or not an operator has commanded the execution of the measuring scan, based on the information inputted from the input unit 13 (step S1). If such a command has been made, predetermined pulse sequence information is provided to the sequencer 5 to allow the measuring scan as described above to be performed with respect to the cardiac chamber of a subject (step S2). Thus, as shown in FIG. 4a, for example, the varying data of the blood flow speed at a desired position in the cardiac chamber can be obtained through the phase shift amount of spin imparted to blood flow.

The host computer 6 then estimates one cycle and the approximate diastole and systole from the obtained variation curve of the blood flow speed (step S3). At the time of this estimation, reference is made to an RR interval which is obtained by back calculation based on the flow direction and a cardiac rate indicated by the blood flow speed data. Thus, the host computer 6 sets and stores a reference time phase (here, the timing when a waveform indicates a peak) and the time phases in the diastole in the varying data of the blood flow speed (step S4).

The host computer 4 then determines whether or not an operator has commanded execution of the preparing scan, based on the information inputted from the input unit 13 (step S5). If the determination is YES, scan conditions, such as blood flow speeds for starting the preparing scan for a plurality of times, required for executing the preparing scan are inputted (step S6). On this occasion, the operator is demanded to specify the blood flow speeds so that the timing for executing the preparing scan may also be included in the diastole.

Under such scanning conditions, a command is given to the sequencer 5 from the host computer 4 to execute the preparing scan over the cardiac chamber (step S7). Along with the preparing scan, the blood flow speed in the cardiac chamber is detected using the PC technique in the same manner as described above to know matching of the blood flow speed with a specified blood flow speed. Every time the result of detection matches with a specified blood flow speed, the preparing scan is executed.

As described above, by performing one or more preparing scans, one or more two-dimensional images of the cardiac chamber for confirming depiction of blood vessels are indicated on the display 12 (step S8).

The host computer 6 then waits for reception of operational information that will be given through the input unit 13, as to which of the displayed images should be designated as a desired image (step S9). An operator thus designates an image having the best contrast of blood flow as the desired image from among the one or more displayed images.

Upon designation of a desired mage by an operator, the host computer 5 specifies and stores the blood flow speed at the time acquisition of the image was commanded (step S10).

Note that, if the preparing scan is determined not to be performed at step S5, a desired blood flow speed is inputted by an operator (steps S11 and S12).

The host computer 6 then stands by while determining, based on the operational information inputted by an operator through the input unit 13, whether or not the imaging scan should be performed (step S13). When the imaging scan is performed, the monitoring scan is started first at a certain interval (step S14). As described above, this monitoring scan is performed by obtaining, with the use of the PC technique, the phase shift amount of spin imparted to blood flow, and converting the phase shift amount into a blood flow speed.

The host computer 6 determines whether or not the blood flow speed detected by the monitoring scan matches the blood flow speed in the diastole which has been set or specified at step S10 or step S11, or whether or not the detected blood flow speed can be regarded to be a blood flow speed close to the specified blood flow speed (step S15). If the determination results in NO, the monitoring scan is performed again. In this way, the monitoring scan is repeated, as shown in FIG. 4B, until the blood flow speed that has been set through the preparing scan or the blood flow speed specified by an operator is obtained.

During the repeated monitoring scan, when a blood flow speed is determined to match or is close to the set value, the host computer 6 allows the sequencer 5 to start data acquisition (main scan) (step S16). As a result, as shown in FIG. 4C, the pulse sequence based, for example, on the three-dimensional FASE technique is started to acquire the MR signal from the cardiac chamber. Based on the MR signal, MR images of various sites including the heart, the abdomen and the lower limb are reconstructed.

As described above, according to the present embodiment, the problems arising from the ECG synchronization technique of the conventional non-contrast MRA can be resolved. In particular, the phase shift amount of spin imparted to blood flow, i.e., the blood flow speed, can be used as a signal alternative to the ECG information, without actually using an ECG measuring device, i.e., without having to mount the ECG sensors on a subject. In this way, the cardiac phase in the diastole can be estimated with precision from such an alternative signal in a pseudo manner. Thus, troubles and burden imposed on a subject accompanying the mounting of the ECG sensors (i.e., electrodes) are mitigated. Moreover, the magnetic resonance imaging system for non-contrast MRA can be provided, which can prevent image quality deterioration due to the mounting of the ECG sensors, and decrease of patient throughput.

Note that various modifications can be made in the first embodiment described above. For example, as a signal or information that is an indicator for enabling estimation of the cardiac phase of a subject, variation in the MR signal obtained from the heart (cardiac chamber) and variation in the size of the cardiac chamber may be used as an alternative to the variation in the blood flow speed in the cardiac chamber (i.e., phase shift amount of spin imparted to blood flow). Such a signal periodically changes through the systole and the diastole, and this also applies to the size of the cardiac chamber. Accordingly, the information on the variation in the MR signal and the variation in the size of the cardiac chamber can be employed as an alternative to the ECG signal, by estimating the diastole from the periodically changing information, and setting a desired time phase of the diastole in the same manner as described above.

Second Embodiment

With reference to FIGS. 5A to 5C to FIGS. 7A and 7B, a second embodiment of the magnetic resonance imaging system according to the present invention is described.

The second embodiment is characterized in that the cardiac phases are estimated by using a coil unit exclusive to a heart rate meter, and on the basis of the intensity of the MR signal acquired by the coil unit. Particularly, in the magnetic resonance imaging system related to the first embodiment described above, the actual site of imaging has been two-dimensionally scanned, as the measuring scan, using the phase contrast technique. Instead, in the present embodiment, an arrangement is so made that a coil unit exclusive to a heart rate meter is mounted on an arm (including fingertips, wrist and joints) of a subject, and the MR signal reflecting the heart rate is acquired from the arm by way of this coil unit.

Figure 5A:
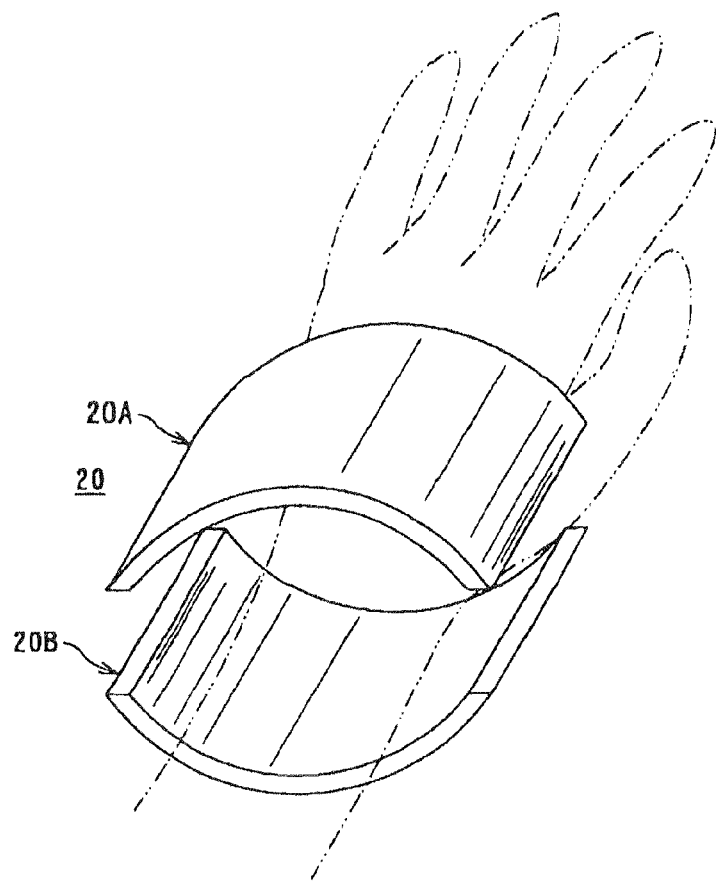
FIGS. 5A to 5C are perspective views for explaining a coil unit exclusive to heart rate measurement, which is used in the magnetic resonance imaging system related to a second embodiment of the present invention.
Figure 5B:
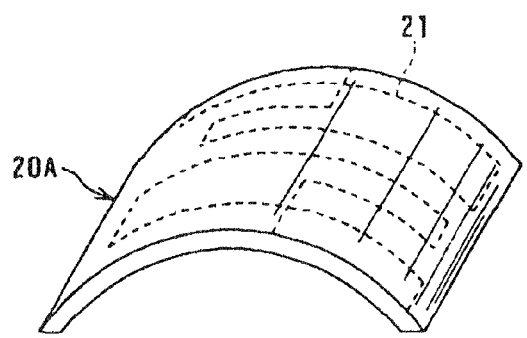
Figure 5C:
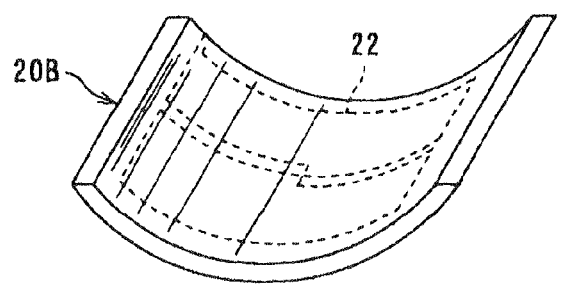

FIGS. 5A to 5C illustrate an appearance of a coil unit 20 exclusive to a heart rate meter, which is mounted on an arm. As shown in FIG. 5A, the coil unit 20 is formed of a nonmagnetic material of substantially an elliptic shape in its entirety, and is divided into two parts, i.e., a first coil member 20A and a second coil member 2B, along its axial direction. The first coil member 20A and the second coil member 20B are mounted, for example, on a subject's wrist from both sides thereof and fastened with a fastener (not shown). The first and the second coil members 20A and 20B are thus mounted around the wrist.

Figure 7A:
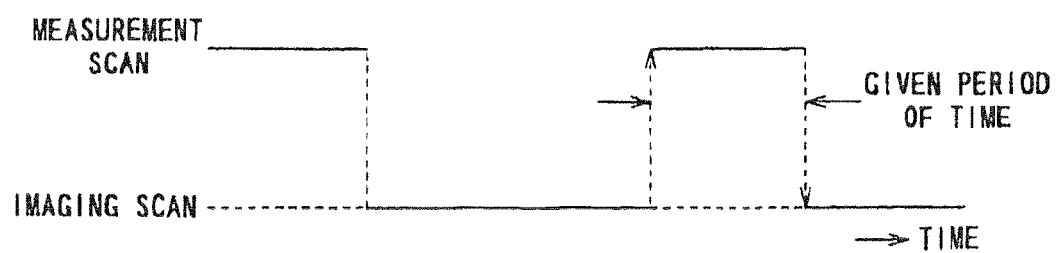
FIGS. 7A and 7B are explanatory diagrams showing execution timing of a measuring scan and an imaging scan in the second embodiment.
Figure 7B:
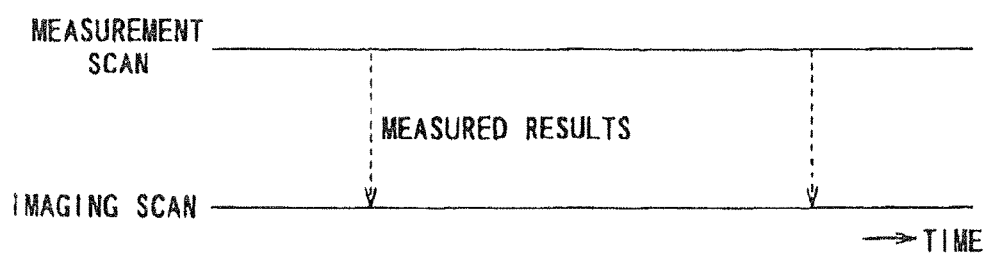

A gradient magnetic field coil 21 and a receiving RF coil 22 are embedded in the first and the second coil members 20A and 20B, respectively. FIG. 7B shows the gradient magnetic field coil 21 alone, and FIG. 7C shows the RF coil 22 alone. Preferably, each of the coils 20A is provided with both the gradient magnetic field coil 21 and the receiving RF coil 22. It suffices, however, that the coil unit 20 should detect only the MR signal from the blood flow whose flow speed varies according to the beat. Thus, the gradient magnetic field coil 21 should only have to generate a one-dimensional gradient magnetic field along the longitudinal direction of the arm. The gradient magnetic field coil 21 therefore is provided only along one axis. As a matter of course, gradient magnetic field coils may be provided along three axial directions which are orthogonal to each other.

A coil unit to be mounted on a fingertip does not have to have the divided structure as described above. It may have a cylindrical fixed structure into which a fingertip can be inserted for mounting.

Note that in the present embodiment, an arm is selected as a site to mount a heart rate meter. This is because, for example, an access can be readily made to a blood vessel which comparatively strongly reflects the cardiac rate of a subject, and a subject may not generally feel so much a burden by mounting the coil unit 20 on the arm. In addition to this, in case an imaging site subjected to actual MRA is a chest or a head, more precise detection of beat can be readily attained since such an imaging site locates comparatively close to the arm.

Figure 6:
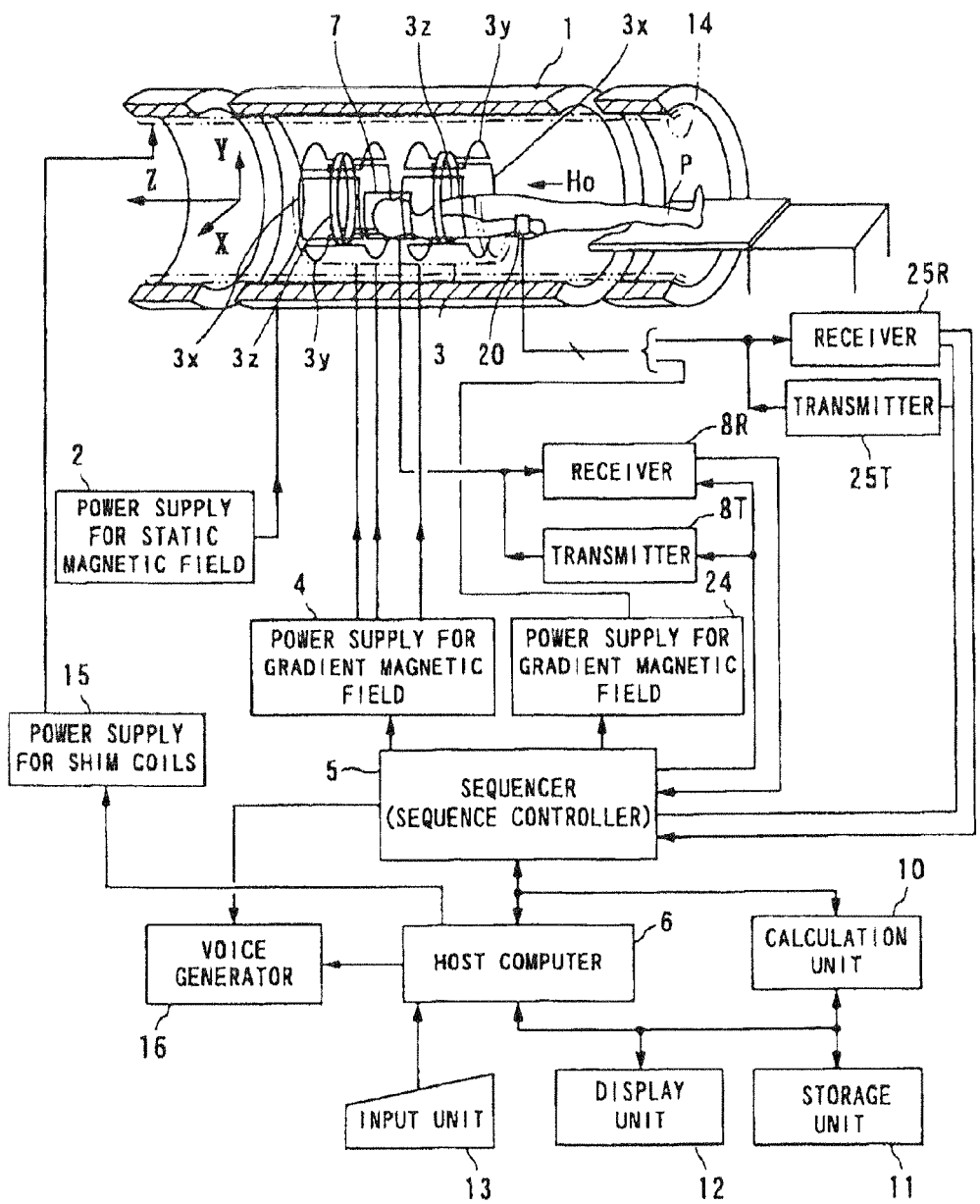
FIG. 6 is a schematic block diagram showing a configuration of the magnetic resonance imaging system related to the second embodiment.

FIG. 6 shows an entire configuration of the magnetic resonance imaging system which performs the measuring scan using the coil unit 20 described above. As shown in the figure, the gradient magnetic field power supply 4, the transmitter 8T and the receiver 8R in the first embodiment described above are used for the preparing scan and the imaging scan. Another gradient magnetic field power supply 24, another transmitter 25T and another receiver 25R, which are under the control of the sequencer 5, are also provided. The gradient magnetic field power supply 24 is connected to the gradient magnetic field coil 21 of the coil unit 20, and the transmitter 25T and the receiver 25R are connected to the RF coil 22 of the coil unit 20.

For the preparing scan and the imaging scan, the sequencer 5 controls the gradient magnetic field power supply 4, the transmitter 8T and the receiver 8R in the same manner as in the first embodiment, based on the pulse sequence information from the host computer 6, while giving instructions for the measuring scan to the gradient magnetic field power supply 24, the transmitter 25T and the receiver 25R. Thus, the sequencer 5 is a common device for both of the scans. Note that, depending on design, the gradient magnetic field power supplies 4 and 24 may be formed as a single unit, the transmitters 8T and 25T may be formed as a single unit, and the receivers 8R and 25R may be formed as a single unit.

As an example, the measuring scan is performed using the phase contrast (PC) technique, in the same manner as described above, by applying flow-encoding pulse in the direction of the gradient magnetic field. This allows for averaged MR signal acquisition from the site where a signal should be acquired. The acquisition is performed again with the polarity of the flow-encoding pulse being reversed to calculate the difference between signal values. Accordingly, the MR signal reflecting the blood flow, in particular, the blood flow in arteries, can be acquired in chronological order. As a result of the acquisition, the same signal variation curve as the one described referring to FIG. 4A can be obtained for measurement (estimation) of the cardiac cycle.

Thereafter, as in the first embodiment, the preparing scan and the imaging scan are performed. Also, the preparing scan is not essential as in the first embodiment.

In particular, in the second embodiment, the timing of performing the measuring scan may be alternated with or in parallel with the imaging scan, not necessarily preceding the imaging scan. This timing is schematically illustrated in FIGS. 7A and 7B. As shown in FIG. 7A, the alternate execution of the measuring scan and the imaging scan means that the measuring scan is performed at every given interval, the result of which being reflected on the imaging scan. For example, when the measuring scan reveals that the cardiac cycle has been accelerated during the imaging scan, some real-time measures, such as timing adjustment of the imaging scan, can be taken. Such measures owe to the sequencer 5. As shown in FIG. 7B, while constantly performing the measuring scan in parallel with the imaging scan, the results of the measuring scan may be reflected on the imaging scan periodically or as required by the imaging scan. In this case, as well, the real-time performance of the measuring scan can be enjoyed.

As described above, the present embodiment can also provide the same operational effects as in the first embodiment described above. In addition, by performing the measuring scan with respect to an arm by using the coil unit 20 exclusive to a heart rate meter, the sequence processing may be simplified, such as use of only one-dimensional gradient magnetic. Since, in the first embodiment, measuring scan has been performed two-dimensionally, the difference between the first and the second embodiments is prominent.

Note that the present invention is not limited to the embodiments described above, but can be implemented in adequately modified other embodiments without departing from the spirit of the present invention set forth in the claims.

What is claimed is:

1. A magnetic resonance imaging (MRI) system comprising:
   a first radio frequency (RF) coil adapted for coupling to a first anatomical portion of a subject and for acquiring a first magnetic resonance (MR) signal from the first anatomical portion, the first MR signal being acquired by a measuring scan using a phase contrast technique;

second RF coil adapted for coupling to a second anatomical portion which is different from the first anatomical portion and for acquiring a second MR signal from the second anatomical portion, the second MR signal being acquired by a non-contrast MRA imaging scan; and one or more computers configured to:

measure blood flow speed of the subject corresponding to each of plural cardiac phases of the subject using the first MR signal acquired by the first RF coil;

estimate a cardiac phase of the subject based on the measured blood flow speed;

image the subject using the non-contrast MRA imaging scan at the estimated cardiac phase; and reconstruct a magnetic resonance image of the subject based on the second MR signal acquired by the non-contrast MRA imaging scan using the second RF coil.

2. The magnetic resonance imaging system according to claim 1, wherein said first RF coil is provided in a vicinity of said second RF coil.

3. The magnetic resonance imaging system according to claim 1, wherein said first RF coil is adapted to be arranged on a chest of said subject.

4. The magnetic resonance imaging system according to claim 1, wherein said first RF coil is adapted to be arranged on an arm of said subject.

5. The magnetic resonance imaging system according to claim 1, wherein acquisition of said magnetic resonance signal with said first RF coil, and acquisition of said magnetic resonance signal with said second RF coil, are performed alternately.

6. The magnetic resonance imaging system according to claim 1, wherein acquisition of said magnetic resonance signal with said first RF coil, and acquisition of said magnetic resonance signal with said second RF coil are performed in parallel.

7. The magnetic resonance imaging system according to claim 1, wherein a monitoring scan is performed to monitor a blood flow speed prior to the non-contrast MRA imaging scan, and the non-contrast MRA imaging scan is started when the blood flow speed monitored by the monitoring scan matches a blood flow speed corresponding to the cardiac phase determined by the data.

8. The magnetic resonance imaging system according to claim 1, wherein said configured one or more computers further configured to:

acquire a magnetic resonance signal during a preparatory scan at a plurality of time phases of said subject;

produce a plurality of preparatory images from the magnetic resonance signal obtained by said preparatory scan;

designate at least one image in said plurality of preparatory images; and acquire an MRI signal from the subject at a cardiac phase determined by the acquired MRI data and a blood flow speed corresponding to the designated image.

9. The magnetic resonance imaging system according to claim 8, wherein said preparatory images are two-dimensional images.

10. A magnetic resonance imaging (MRI) signal acquisition method comprising:

measuring blood flow speed of a subject corresponding to each of plural cardiac phases of the subject based on magnetic resonance signals acquired from a first region of the subject coupled to a first radio frequency (RF) coil using a phase contrast technique;

estimating a cardiac phase of the subject based on the measured blood flow speed;

imaging the subject by acquiring MRI data of the subject from a different second region of the subject coupled to a second RF coil using a non-contrast MRA imaging scan at the estimated cardiac phase; and reconstructing a magnetic resonance image of the subject based on a magnetic resonance signal acquired by the non-contrast MRA imaging scan.

11. The acquisition method according to claim 10, wherein said first RF coil is accommodated in a coil unit exclusive to cardiac phase estimation, which is integrated into a gradient magnetic field coil for generating gradient magnetic field, which gives spatial position information to a static magnetic field where said subject is placed.

12. The acquisition method according to claim 11, wherein said gradient magnetic field coil is a gradient magnetic field coil for generating one-dimensional gradient magnetic field.

* * * * *